(12) United States Patent
He et al.

(10) Patent No.: US 11,278,542 B2
(45) Date of Patent: Mar. 22, 2022

(54) USE OF NICOTINAMIDE COMPOSITION IN PREPARATION OF DRUG FOR TREATING HAND-FOOT SKIN REACTION INDUCED BY SORAFENIB

(71) Applicant: ZHEJIANG UNIVERSITY, Hangzhou (CN)

(72) Inventors: Qiaojun He, Hangzhou (CN); Bo Yang, Hangzhou (CN); Peihua Luo, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/612,770

(22) PCT Filed: Oct. 31, 2018

(86) PCT No.: PCT/CN2018/113216
§ 371 (c)(1),
(2) Date: Nov. 12, 2019

(87) PCT Pub. No.: WO2020/029441
PCT Pub. Date: Feb. 13, 2020

(65) Prior Publication Data
US 2021/0330659 A1 Oct. 28, 2021

(30) Foreign Application Priority Data
Aug. 7, 2018 (CN) .......................... 201810891108.2

(51) Int. Cl.
*A61K 31/455* (2006.01)
*A61P 17/00* (2006.01)
*A61K 31/44* (2006.01)

(52) U.S. Cl.
CPC ............ *A61K 31/455* (2013.01); *A61K 31/44* (2013.01); *A61P 17/00* (2018.01)

(58) Field of Classification Search
CPC ........ A61K 31/455; A61K 31/44; A61P 17/00
See application file for complete search history.

(56) References Cited

FOREIGN PATENT DOCUMENTS

| | | |
|---|---|---|
| CN | 107362362 A | 11/2017 |
| EP | 2712613 A | 4/2014 |
| WO | 2004006887 A | 1/2004 |
| WO | 2010072420 A | 7/2010 |

OTHER PUBLICATIONS

International Search Report (PCT/CN2018/113216); dated May 9, 2019.
"s-HBEGF/SIRT1 circuit-dictated crosstalk between vascular endothelial cells and keratinocytes mediates sorafenib-induced hand-foot skin reaction that can be reversed by nicotinamide" (Apr. 15, 2020).

*Primary Examiner* — Kevin E Weddington
(74) *Attorney, Agent, or Firm* — W&G Law Group

(57) ABSTRACT

The present disclosure provides a use of a nicotinamide composition in preparation of a drug for treating hand-foot skin reaction (HFSR) induced by sorafenib, the composition being consisted of nicotinamide and sorafenib in a dosage ratio of 2:3. The composition provided by the present disclosure can alleviate the HFSR caused by excessive keratinization induced by sorafenib. This protective effect is achieved by inhibiting HB-EGF/SIRT1 pathway. The present disclosure provides a mechanism of sorafenib-induced HFSR, i.e., the excessive activation of the HB-EGF/SIRT1 pathway, thereby providing a theoretical foundation for clinical research of sorafenib-induced HFSR. The present disclosure also provides a drug that can effectively treat sorafenib-induced HFSR, thereby greatly broadening the clinical application of sorafenib. Nicotinamide is highly clinically feasible due to its moderate price, and thus can be prepared in any suitable formulation according to the requirements.

3 Claims, 2 Drawing Sheets

HBEGF-SIRT1 signaling pathway is involved in sorafenib-induced HFSR

SIRT1 inhibitor (nicotinamide) alleviates sorafenib-induced HFSR

USE OF NICOTINAMIDE COMPOSITION IN PREPARATION OF DRUG FOR TREATING HAND-FOOT SKIN REACTION INDUCED BY SORAFENIB

CROSS-REFERENCE TO RELATED APPLICATIONS

The present application is based on International Application No. PCT/CN2018/113216 filed Oct. 31, 2018, which claims priority to Chinese Patent Application No. 2018108911082, filed on Aug. 7, 2018, the contents of which are incorporated herein by reference in its entirety.

TECHNICAL FIELD

The present disclosure belongs to the pharmaceutical field, and relates to a use of a nicotinamide composition in preparation of a drug for treating hand-foot skin reaction (HFSR) induced by sorafenib.

BACKGROUND

Sorafenib is a tyrosine kinase inhibitor (TKI) against the vascular endothelial growth factor (VEGF) family, belonging to the first-line drugs fin the treatment of advanced hepatocellular carcinoma and renal cell carcinoma, which can significantly prolong the progressive-free-survival (PFS) of the patients. However, sorafenib has severe toxic side effects, the most common of which is the hand-foot skin reaction (HFSR) clinically characterized by hyperkeratosis, with a prevalence of up to 60%. Although sorafenib-induced HFSR is generally not a life-threatening side effect, it affects the patient's quality of life and may also result in a dosage adjustment or treatment interruption that ultimately threatens the patient's life.

Due to the unknown molecular mechanism of sorafenib-induced HFSR, there is no efficient clinical strategy to intervene this side effect. For patients with mild HFSR, keratolytics or emollient can be used to relieve the symptoms. Regarding patients with severe HFSR during the course of medication, it is necessary to adjust the dosage of the drug or even discontinue the treatment. However, the therapies mentioned above only can relieve the symptoms to a certain extent, rather than cure sorafenib-induced HFSR. Therefore, it is important to figure out the molecular mechanism of sorafenib-induced HFSR and find a suitable intervention strategy based on the molecular mechanism, to alleviate the HFSR induced by sorafenib.

Applicants have found through researches that sorafenib can induce vascular endothelial cells (HUVECs) to secrete heparin-binding epidermal growth factor (HB-EGF), which activates the HB-EGF/SIRT1 signaling pathway, and accelerates a keratinization process of keratinocytes (HaCaT), thereby ultimately leading to HFSR. Since SIRT1 plays a pivotal role in sorafenib-induced HFSR, a combination of SIRT1 inhibitors with sorafenib may significantly relieve sorafenib-induced HFSR.

Nicotinamide, as a member of vitamin B family, is a common SIRT1 inhibitor. Nicotinamide can be mainly used for the prevention and treatment of pellagra, stomatitis and glossitis, as well as for the treatment of coronary heart disease, viral myocarditis, rheumatic heart disease, etc. However, it has not been reported that nicotinamide can be used to treat the HFSR induced by sorafenib.

SUMMARY

The present disclosure aims to provide a use of a nicotinamide composition in preparation of a drug for treating HFSR induced by sorafenib, in which the composition consists of nicotinamide and sorafenib, and nicotinamide and sorafenib is combined in a dosage ratio of 2:3.

They are combined in the dosage ratio of 2:3 on the cell model, i.e., nicotinamide 10 μM: sorafenib 15 μM.

Nicotinamide has a chemical name of 3-pyridinecarboxamide, a molecular formula of $C_6H_6N_2O$, and a molecular weight of 122.13. Sorafenib has a chemical name of 4-{4-[({4-chloro-3-(trifluoromethyl)phenyl]amino}carbonyl)amino]phenoxy}-N-methylpyridine-2-carboxamide, a molecular formula of $C_{21}H_{16}ClF_3N_4O_3$, and a molecular weight of 464.83.

The mechanism of nicotinamide alleviating HFSR induced by sorafenib is provided by the present disclosure: sorafenib activates the HB-EGF/SIRT1 pathway and accelerates the keratinization process, which in turn leads to the HFSR; SIRT1 inhibitor, nicotinamide, blocks the activation of this pathway, thereby alleviating sorafenib-induced HFSR. Therefore, nicotinamide composition can be used to treat sorafenib-induced HFSR.

The drug is in a liquid formulation or a solid formulation, and is prepared with a composition of nicotinamide and sorafenib and a pharmaceutically acceptable adjuvant, including oral solid preparation, oral liquid preparation, injection, lyophilized powder injection, infusion, patch, ointment, gel, soft capsule or suppository.

The composition of a SIRT1 inhibitor, nicotinamide, and an antineoplastic drug, sorafenib, provided by the present disclosure can alleviate HFSR caused by a hyperkeratinization induced by sorafenib. This protective effect is achieved by inhibiting the HB-EGF/SIRT1 pathway. The present disclosure has the following advantages of: (1) providing a mechanism of sorafenib-induced HFSR, i.e., an excessive activation of the HB-EGF/SIRT1 pathway, thereby providing a theoretical foundation for clinical research of the sorafenib-induced HFSR; (2) providing a drug that can effectively treat sorafenib-induced HFSR, thereby greatly broadening the clinical application of sorafenib, and (3) providing a high clinical feasibility as nicotinamide is moderately priced, and can be prepared in suitable formulations according to the requirements.

DESCRIPTION OF EMBODIMENTS

The present disclosure is described in detail as follow in combination with the accompanying drawings and embodiments.

Embodiment 1

Figure 1:
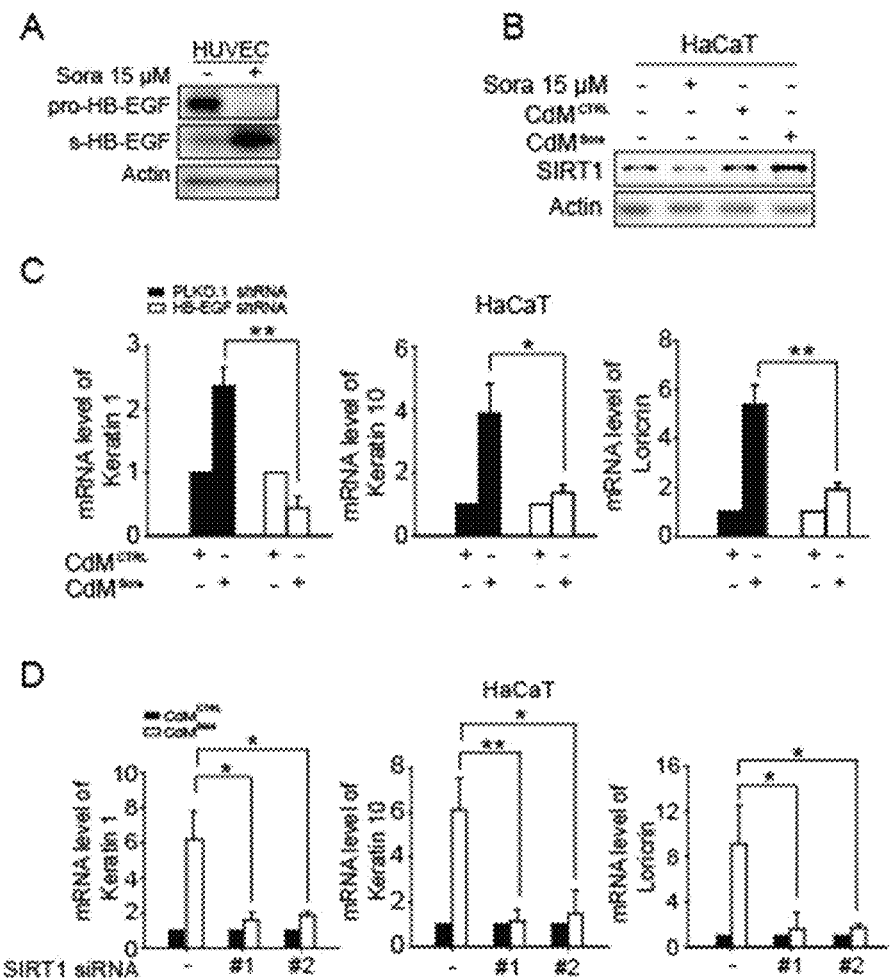
FIG. 1 illustrates an effect of sorafenib on HB-EGF/SIRT1 signaling pathway and an effect of inhibition of the pathway on keratinization progress.

HUVEC cells were administrated with 15 μM sorafenib. After that, the cells and the culture medium were separately collected, and the culture medium is concentrated. Then, pro-HB-EGF, an inactive cross-membrane structure in cell lysate and s-HB-EGF proteins, an active free form in the culture medium were detected by western blot. According to the results shown in FIG. 1A, the expression level of the HB-EGF protein in the cells was down-regulated, and the expression of HB-EGF protein in the culture medium was increased. HUVEC culture medium treated with sorafenib, as a conditioned medium, was applied to HaCaT cells, and the expression of SIRT1 in the cells was detected. According to experimental results shown in FIG. 1B, the expression of SIRT1 was up-regulated in the HaCaT cells. After HUVEC cells with HB-EGF knocked out were constructed, the culture medium obtained after administrated with sorafenib was administrated to the HaCaT cells, and mRNA levels of the keratinization progress indicators, i.e., keratin 1, keratin 10 and Loricrin, were detected. According to experimental results shown in FIG. 1C, after HB-EGF was knocked out, the mRNA levels of the three keratins were down-regulated. The HUVEC culture medium added with sorafenib, as the conditioned medium, was applied to the HaCaT cells in which SIRT1 was knocked out, and the mRNA levels of the three keratins were detected. According to experimental results shown in FIG. 1D, the mRNA levels of the three keratins were also down-regulated. The above experimental results indicate that sorafenib accelerates the keratinization progress, such that the cause of the HFSR is due to an excessive activation of the HB-EGF/SIRT1 pathway.

Embodiment 2

Figure 2:
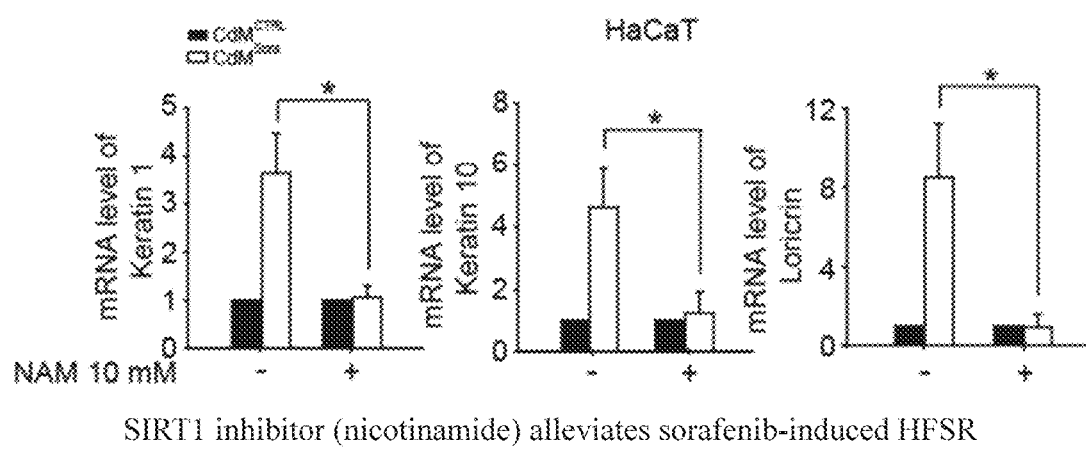
FIG. 2 illustrates the effect on the keratinization progress after HaCaT cells were incubated with HUVEC cell culture medium, as a conditioned medium, which is treated with nicotinamide and sorafenib.

In an in vitro cell experimental model, HUVEC cells were administrated with 15 μM sorafenib alone, and 15 μM sorafenib together with 10 μM nicotinamide, respectively. After 24 hours, the culture medium was collected as a conditioned medium for HaCaT cells, and the HaCaT cells were collected 24 hours later for the detection of mRNA levels of three keratins. Results of the study are shown in FIG. 2: compared with the HUVEC medium treated with sorafenib alone, the mRNA levels of the three keratins in the HaCaT cells after the administration of HUVEC medium treated with both nicotinamide and sorafenib were significantly down-regulated. It indicates that nicotinamide can inhibit the acceleration of keratinization progress caused by sorafenib.

What is claimed is:

1. A method for treating hand-foot skin reaction induced by sorafenib, comprising administrating a drug to a subject, wherein the drug comprises a composition consisting of nicotinamide and sorafenib, where in nicotinamide has a chemical name of 3-pyridinecarboxamide, a molecular formula of $C_6H_6N_2O$, and a molecular weight of 122.13, and sorafenib has a chemical name of 4-{4-[({4-chloro-3-(trifluoromethyl)phenyl]amino}carbonyl)amino]phenoxy}-N-methylpyridine-2-carboxamide, a molecular formula of $C_{21}H_{16}ClF_3N_4O_3$, and a molecular weight of 464.83.

2. The method according to claim 1, wherein in the composition, a dosage ratio of nicotinamide to sorafenib is 2:3.

3. The method according to claim 1, wherein the drug is prepared with a composition of nicotinamide and sorafenib and a pharmaceutically acceptable adjuvant, and the drug is in a liquid formulation or a solid formulation.

* * * * *